(12) United States Patent
Abell et al.

(10) Patent No.: US 6,440,714 B2
(45) Date of Patent: Aug. 27, 2002

(54) TYR$^{393}$ AND TYR$^{398}$ MUTANTS OF MONOAMINE OXIDASE B

(75) Inventors: Creed W. Abell, Austin; Binhau Zhou, Sugarland; Sau-Wah Kwan, Austin, all of TX (US); Bo Wu, Urbana, IL (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/822,624

(22) Filed: Mar. 30, 2001

Related U.S. Application Data

(60) Provisional application No. 60/193,178, filed on Mar. 30, 2000.

(51) Int. Cl.$^7$ .......................... C12N 9/06; C12N 15/00; C07H 21/04
(52) U.S. Cl. .................. 435/191; 536/23.2; 435/320.1
(58) Field of Search ................................ 435/189, 191; 536/23.2

(56) References Cited

FOREIGN PATENT DOCUMENTS

WO     WO 01/75080 A1   *   10/2001

OTHER PUBLICATIONS

Cesura A. M. et al, Eur. J. Biochem. Investigation on the structure of the active site of monoamine oxidase–B by affinity labeling with the selective inhibitor lazemide and by site–directed mutagenesis, 1996, 236, 996–1002.*

* cited by examiner

Primary Examiner—Tekchand Saidha
Assistant Examiner—Malgorzata A. Walicka
(74) Attorney, Agent, or Firm—Benjamin Aaron Adler

(57) ABSTRACT

Monoamine oxidase A and B (MAO A and B) are major neurotransmitter- and xenobiotic-metabolizing enzymes that are thought to play a role in psychiatric and neurological disorders. These isozymes have a high degree of identity in their nucleotide deduced amino acid sequences, but are encoded by different genes on the X-chromosome. Previous studies on MAO B have shown that FAD binds both noncovalently and covalently to specific amino acid residues that reside in highly conserved regions of MAO A and B. In the instant invention, it is demonstrated that the aromatic moieties at Tyr$^{393}$ and Tyr$^{398}$, which are located on each side of the covalent FAD binding residue (Cys$^{397}$) participate in covalent FAD binding, and the generation of catalytically active MAO B.

7 Claims, 6 Drawing Sheets

```
hMAO A    Q Y S G G C Y T A Y F - - P P G I M T Q Y G R V    (401-422) (SEQ ID NO: 6)
rMAO A    Q Y S G G C Y T A Y F - - P P G I M T Q Y G R V    (401-422) (SEQ ID NO: 7)
bMAO A    Q Y S G G C Y T A Y F - - P P G I M T Q Y G R V    (401-422) (SEQ ID NO: 8)
hMAO B    Q Y S G G C Y T A Y F - - P P G I M T Q Y G R V    (392-413) (SEQ ID NO: 9)
rMAO B    Q Y S G G C Y T A Y F - - P P G I M T Q Y G R V    (392-413) (SEQ ID NO: 10)
          e e e   e e e                           e e e

CvFCSD    Y Y T - - C Y L S N E V I G G D R K L E S I K H    ( 39-60 ) (SEQ ID NO: 11)
          e e e   e e e                           e e e
```

Fig. 1A

```
Ao6-HDNO  V R S G G H N P N G Y A T N D G G I V L D L R L M N S    ( 66-92 ) (SEQ ID NO: 12)
bSDHA     T R S - - H T V A A Q - - - - G G I N A A A L - - - -    ( 97-115) (SEQ ID NO: 13)
ScSDHA    T R S - - H T V A A Q - - - - G G I N A A A L - - - -    ( 87-105) (SEQ ID NO: 14)
EcSDHA    T R S - - H T V S A Q - - - - G G I H T V A L - - - -    ( 42-60 ) (SEQ ID NO: 15)
BsSDHA    K R S - - H S V C A Q - - - - G G I N G A V - - - -     ( 38-55 ) (SEQ ID NO: 16)
PvFRDA    M R S - - H T V A A E - - - - G G - S A A A V - - - -    ( 42-59 ) (SEQ ID NO: 17)
EcFRDA    M R S - - H T V A A E - - - - G G - S A A A V - - - -    ( 42-59 ) (SEQ ID NO: 18)
WsFRDA    K R S - - H S A A A A Q - - - G G M Q A S L - - - -     ( 40-58 ) (SEQ ID NO: 19)
```

Fig. 1B

| cDNA | Mutagenic Primer | Side Chain |
|---|---|---|
| Wild-type | 393 |  |
| (SEQ ID NO: 20) | W C E E Q Y S G G C Y T T Y F P P |  |
| (SEQ ID NO: 21) | TGGTGTGAGGAGCAGT<u>ACT</u>CTGGGGGCTGCTACACAACTTATTCCCCCT |  |
|  | <u>Sca I</u> |  |
| Y393F | F |  |
|  | GGTGTGAGGAGCAGTtCTCTGGGGGCTG (SEQ ID NO: 22) | —CH$_2$—⌬ |
| Y393A | A |  |
|  | GGTGTGAGGAGCAGgcCTCTGGGGGCTG (SEQ ID NO: 23) | —CH$_3$ |
| Wild-type | 394 |  |
| (SEQ ID NO: 20) | W C E E Q Y S G G C Y T T Y F P P |  |
| (SEQ ID NO: 21) | TGGTGTGAGGAGCAGTACT<u>CT</u>GGGGGCTGCTACACAACTTATTCCCCCT |  |
|  | <u>Sca I</u> |  |
| S394A | A |  |
|  | GGAGCAGTACgCTGGGGGCTG (SEQ ID NO: 24) | —CH$_3$ |
| Wild-type | 398 |  |
| (SEQ ID NO: 20) | W C E E Q Y S G G C Y T T Y F P P |  |
| (SEQ ID NO: 21) | TGGTGTGAGGAGCAGTACTCTGGGGGCTGCTTCACTAC<u>GT</u>ATTCCCCCT |  |
|  | <u>SnaB I</u> |  |
| Y398F | F |  |
|  | GGGCTGCTtCACTAC<u>g</u>TATTTCCCCC (SEQ ID NO: 25) | —CH$_2$—⌬ |
| Y398A | A |  |
|  | CTGGGGGCTGC<u>gc</u>aACAACTTATTTCCC (SEQ ID NO: 26) | —CH$_3$ |
|  | <u>Fsp I</u> |  |

TYR³⁹³ AND TYR³⁹⁸ MUTANTS OF MONOAMINE OXIDASE B

CROSS-REFERENCE TO RELATED APPLICATION

This non-provisional patent application claims benefit of provisional patent application U.S. Ser. No. 60/193,178, filed Mar. 30, 2000, now abandoned.

FEDERAL FUNDING LEGEND

This invention was produced in part using funds obtained through the National Institutes of Health research grant NS24932 and training grant AA07471. Consequently, the federal government has certain rights in this invention.

BACKGROUND OF THE INVENTION

1. Field of the Invention

The present invention relates generally to neurobiology. More specifically, the present invention relates to molecular engineering of monoamine oxidases to determine those domains that play a role in metabolizing cellular neurotransmitters and vasoamines.

2. Description of the Related Art

Monoamine oxidase A and B (MAO A and B, EC 1.4.3.4) are integral covalent flavoproteins of the outer mitochondrial membrane in almost all tissues of mammals (1). MAO A and B catalyze the oxidative deamination of biogenic and vasoactive amines and the oxidation of xenobiotics (2, 3). These isozymes play important roles in regulating the intracellular level of various amines in the central nervous system and peripheral tissues of mammals and in protecting those cells and neurons that non-specifically take up neurotransmitters where they have no legitimate physiological function (4). Several psychiatric and neurological disorders (i.e., Parkinson's disease, depression, and alcoholism) have been linked to these enzymes (5–7).

MAO A and B are distinct polypeptides, but they have a high degree of identity in their nucleotide and deduced amino acid sequences (8). They also differ in substrate and inhibitor preferences and in cell and tissue distributions (4, 10–13). One FAD molecule is covalently linked at $Cys^{397}$ in each subunit (58.8 kDa) of human MAO A and B (9). Previous studies demonstrated that there are two FAD binding sites near the N-terminus (residues 6–34 and 41–45) that are required for both covalent and noncovalent binding of FAD and the generation of MAO B catalytic activity (14–18). In contrast, variants with substituted residues near the middle of the sequence (residues 222–227) can bind FAD noncovalently but not covalently. These variants also have reduced MAO B activities (18).

Based on these observations, it was proposed that FAD is coupled to the MAO B polypeptide in a stepwise process, beginning with the FAD-binding sites near the N-terminus where an initial topological dock for FAD is provided (18). FAD is then delivered to the FAD binding sites in the middle of the sequence to provide another topological dock that further secures FAD. Finally, FAD is delivered to $Cys^{397}$ in a position which places the 8α-methyl group of the isoalloxazine ring of FAD in close proximity to the thiol group of $Cys^{397}$ to facilitate covalent flavinylation.

The prior art is deficient in identifying the active site of the monoamine oxidase (MAO) B enzyme and the effect that mutations to this site have on enzyme activity and the regulation of neuro- and vaso-amines. The present invention fulfills this long-standing need and desire in the art.

SUMMARY OF THE INVENTION

Monoamine oxidase A and B (MAO A and B) are major neurotransmitter- and xenobiotic-metabolizing enzymes that are thought to play a role in psychiatric and neurological disorders. These isozymes have a high degree of identity in their deduced amino acid sequences, but are encoded by different genes on the X-chromosome. Previous studies on MAO B have shown that FAD binds both noncovalently and covalently to specific amino acid residues that reside in highly conserved regions of MAO A and B.

Comparison of the deduced amino acid sequences of MAO A and B from different species (8, 22–25) reveals three highly conserved regions. These regions reside near the N-terminus, in the middle of the polypeptide, and on each side of the covalent FAD binding residue ($Cys^{397}$) in MAO B. It is hypothesized that the highly conserved region flanking $Cys^{397}$ also plays a role in the covalent binding of FAD. This notion is supported by Wouters & Baudoux (20), who constructed the first partial three-dimensional model of human MAO A based on a combination of primary sequence analysis, secondary structure determination, fold recognition studies, and knowledge-based modeling. This model predicted that $Tyr^{407}$ (corresponding to $Tyr^{398}$ in MAO B) is the only amino acid residue that resides in close proximity to the isoalloxazine ring of FAD in the highly conserved region flanking the covalent FAD binding residue ($Cys^{406}$) in MAO A. Furthermore, Mauch et al. (21) found that $Arg^{67}$ in the sequence $Arg^{67}$-$Ser^{68}$-$Gly^{69}$–$Gly^{70}$ (SEQ ID No.2), which immediately precedes the covalent FAD binding residue ($His^{71}$), is obligatory for covalent flavinylation of 6-hydroxy-D-nicotine oxidase (6-HDNO). This sequence pattern has also been found in several other flavoproteins with a covalent histidyl(N3)-8α-FAD linkage (FIG. 1B) (21). It is proposed herein that the sequence $Tyr^{393}$-$Ser^{394}$-$Gly^{395}$-$Gly^{396}$ (SEQ ID No. 3) immediately preceding the covalent FAD binding residue ($Cys^{397}$) plays a similar role in MAO B as does $Arg^{67}$-$Ser^{68}$-$Gly^{69}$-$Gly^{70}$ (SEQ ID No.: 2) in 6-HDNO (FIG. 1). To test this hypothesis, variants of human MAO B were made at $Tyr^{393}$, $Ser^{394}$ and $Tyr^{398}$ to determine if these residues participate in the covalent flavinylation of human MAO B. Analysis of these variants demonstrated that the aromatic moieties at $Tyr^{393}$ and $Tyr^{398}$ are essential for covalent FAD binding and MAO B catalytic activity.

In this study, it is demonstrated that the aromatic moieties at $Tyr^{393}$ and $Tyr^{398}$, which are located on each side of the covalent FAD binding residue ($Cys^{397}$) participate in covalent FAD binding, and the generation of catalytically active MAO B. Based on these results and a three-dimensional model of MAO A (20), it is proposed that two antiparallel β-strands flank the covalent FAD binding residue (a cysteine) in flavoproteins with a covalent cysteinyl(S)-8α-FAD linkage and that this structural motif plays an important role in covalent FAD binding in MAO B.

One object of the present invention is to provide isolated, genetically-engineered MAO B enzymes having at least one amino acid substitution for amino acids near the wild type MAO B flavinylation site, where the wild type amino acid is Tyrosine at position 393, Tyrosine at position 398 and Serine at position 394. The present invention additionally provides isolated DNAs that encode these genetically-engineered MAO B enzymes, and plasmids containing these DNAs along with regulatory elements necessary for expression of these DNAs in a cell.

Specific embodiments of this object of the present invention include the following substitutions: where if the wild type amino acid is Tyrosine 393, the amino acid substitution is Alanine or Phenylalanine; where if the wild type amino acid is Tyrosine 398, the amino acid substitution is Alanine or Phenylalanine; and, where the wild type amino acid is Serine 394, the amino acid substitution is Alanine.

An additional object of the present invention is to provide pharmaceutical compositions which interact with the active site of MAO B. Specific compositions include derivatives of active site components, such as FAD, 2'-deoxy FAD and 3'-deoxy FAD, and derivatives of mechanism-based inhibitors that belong to the acetylenic and cyclopropyl amine classes.

Additionally, an object of the present invention is to provide a method for regulating MAO B comprising the step of mutating an amino acid in the MAO B active site. Specifically, the amino acid to be mutated is selected from the wild type amino acids Tyr 393, Tyr 398, or Ser 394.

Another object of the present invention is to provide a description of the active site of monoamine oxidase B, such that pharmaceutical compositions can be designed to interact with the active site. Specific embodiments of this object of the invention include 2'-deoxy FAD, 3'-deoxy FAD, and derivatives of deprenyl (phenylisopropyl-methylproinylamine) and trans-phenylcyclopropylamine. Molecular modeling is applied to determine which derivatives are most likely to interact with components in the active site of the enzyme.

Other and further aspects, features, and advantages of the present invention will be apparent from the following description of the presently preferred embodiments. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A and 1B show the alignment of sequences flanking the covalent FAD binding residue (a cysteine or a histidine) in a group of flavoproteins with a covalent cysteinyl(S)-8α-FAD linkage or with a covalent histidyl (N3)-8α-FAD linkage.

FIG. 1A is of the alignment of sequences flanking the covalent FAD binding residue in the flavoproteins with a covalent cysteinyl(S)-8α-FAD linkage. The sequences are: hMAO A, human MAO A (8); rMAO A, rat MAO A (22, 23); bMAO A, bovine MAO A (24); hMAO B, human MAO B (8); rMAO B, rat MAO B (25); and CvFCSD, C. vinosum flavocytochrome c-sulfide dehydrogenase (26). The covalent FAD binding residue (a cysteine) is highlighted. The other conserved residues are boxed. The two β-strands flanking the covalent FAD binding residue ($Cys^{42}$) in the crystallographic structure of FCSD (26, 27) and the two predicted β-strands flanking the covalent FAD binding residue ($Cys^{406}$ in MAO A, and $Cys^{397}$ in MAO B) in MAO A and B from different species (20) are also exhibited, where "e" stands for β-strand.

FIG. 1B shows the alignment of sequences flanking the covalent FAD binding residue in the flavoproteins with a covalent histidyl(N3)-8α-FAD linkage. The sequences are:

Ao6-HDNO, A. oxidans 6-hydroxy-D-nicotine oxidase (28); bSDHA, bovine succinate dehydrogenase (29); ScSDHA, S. cerevisiae SDHA (30); EcSDHA, E. coli SDHA (31); B. subtilis SDHA (32); PvFRDA, P. vulgaris fumarate reductase (33); ECFRDA, E. coli FRDA (34); WsFRDA, W. succinogenes FRDA (35). The covalent FAD binding residue (a histidine) is highlighted. The other conserved residues are boxed. The sequences were aligned manually in this figure.

FIG. 2 shows the nucleotide sequences of mutagenic primers used in site-directed mutagenesis of human MAO B. Lowercase letters indicate base substitutions. The codons for wild-type and mutants at $Tyr^{393}$, $Ser^{394}$ and $Tyr^{398}$ are indicated by a single line above the nucleotides. Base substitutions which do not alter the amino acid coding sequence were also included in each mutagenic primer to create a new restriction site, or delete an existing restriction site (double underline) for the purpose of screening. Side chains corresponding to amino acid substitutions are also shown.

Figure 3:
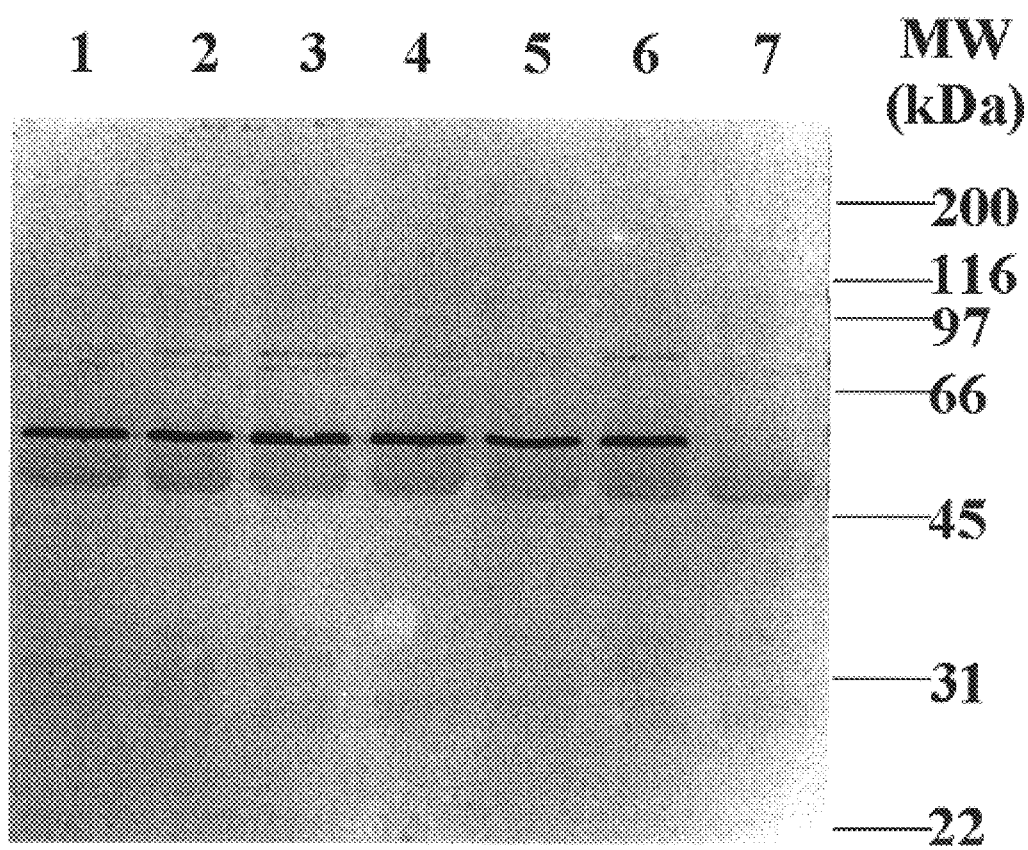

FIG. 3 present the results from Western Blot analysis of wild-type and mutant MAO B. cDNAs expressing each were transfected into COS-7 cells. Before immunoprecipitation with a goat anti-MAO B polyclonal antibody, expressed wild-type and variant MAO B enzymes were adjusted to equal concentrations (based on ELISA). Immunoprecipitated enzymes were then separated on 10% SDS-PAGE, transferred to a nitrocellulose membrane, and analyzed by western blotting using the MAO B-specific monoclonal antibody, MAO B-1C2. Lane 1: wild-type MAO B; lane 2: Y393F MAO B; lane 3: Y393A MAO B; lane 4: Y398F MAO B; lane 5: Y398A MAO B; lane 6: S394A MAO B; lane 7: untransfected COS-7 cells.

Figure 4A:
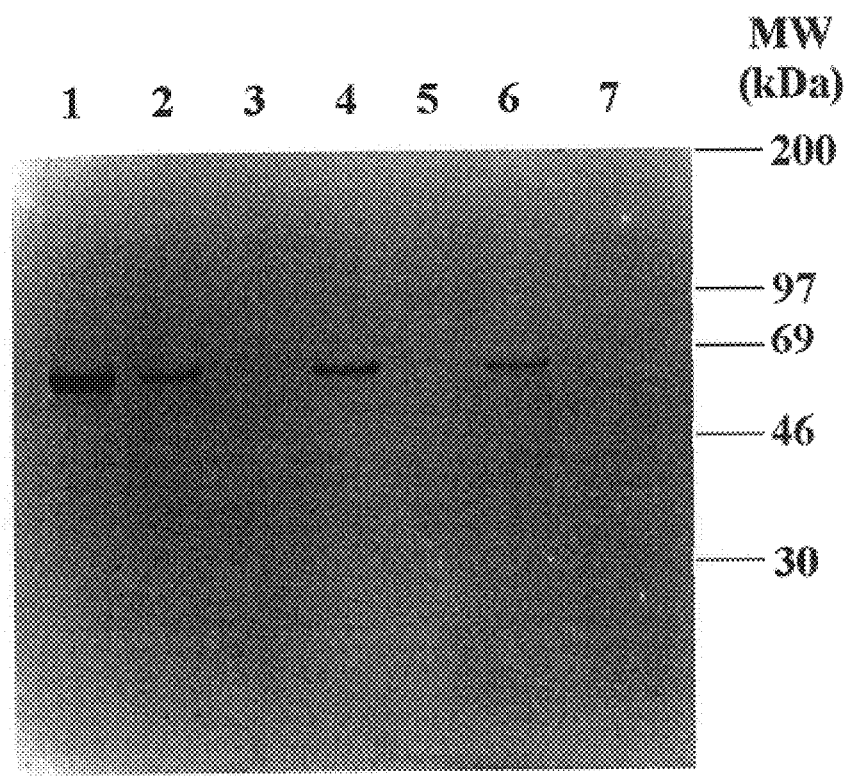
Figure 4B:
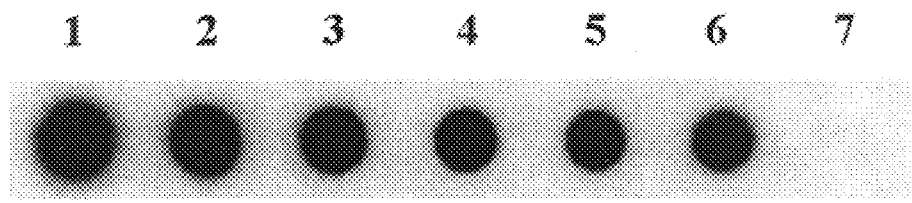

FIGS. 4A and 4B show the effect of site-directed mutagenesis at $Tyr^{393}$, $Ser^{394}$ and $Tyr^{398}$ on FAD-binding of MAO B.

FIG. 4A shows fluorography of SDS-PAGE. Wild-type and mutant cDNAs were transfected in riboflavin-depleted COS-7 cells with the addition of exogenous [$^{14}C$] FAD during electroporation. Expressed wild-type and variant MAO B enzymes were adjusted to equal concentrations based on ELISA before immunoprecipitation. The immunoprecipitated enzymes were separated on 10% SDS-PAGE and subjected to fluorography. Lane 1: wild-type MAO B; lane 2: Y393F MAO B; lane 3: Y393A MAO B; lane 4: Y398F MAO B; lane 5: Y398A MAO B; lane 6: S394A MAO B; and lane 7: untransfected COS-7 cells.

In FIG. 4B, expressed wild-type and variant MAO B enzymes at equal concentration (based on ELISA) were immunoprecipitated, eluted with glycine buffer, and subjected to dot-blot analysis. The dried nitrocellulose membrane of dot-blotting was then subjected to autoradiography. Dot 1: wild-type MAO B; dot 2: Y393F MAO B; dot 3: Y393A MAO B; dot 4: Y398F MAO B; dot 5: Y398A MAO B; and dot 6: S394A MAO B; dot 7: untransfected COS-7 cells.

Figure 5:
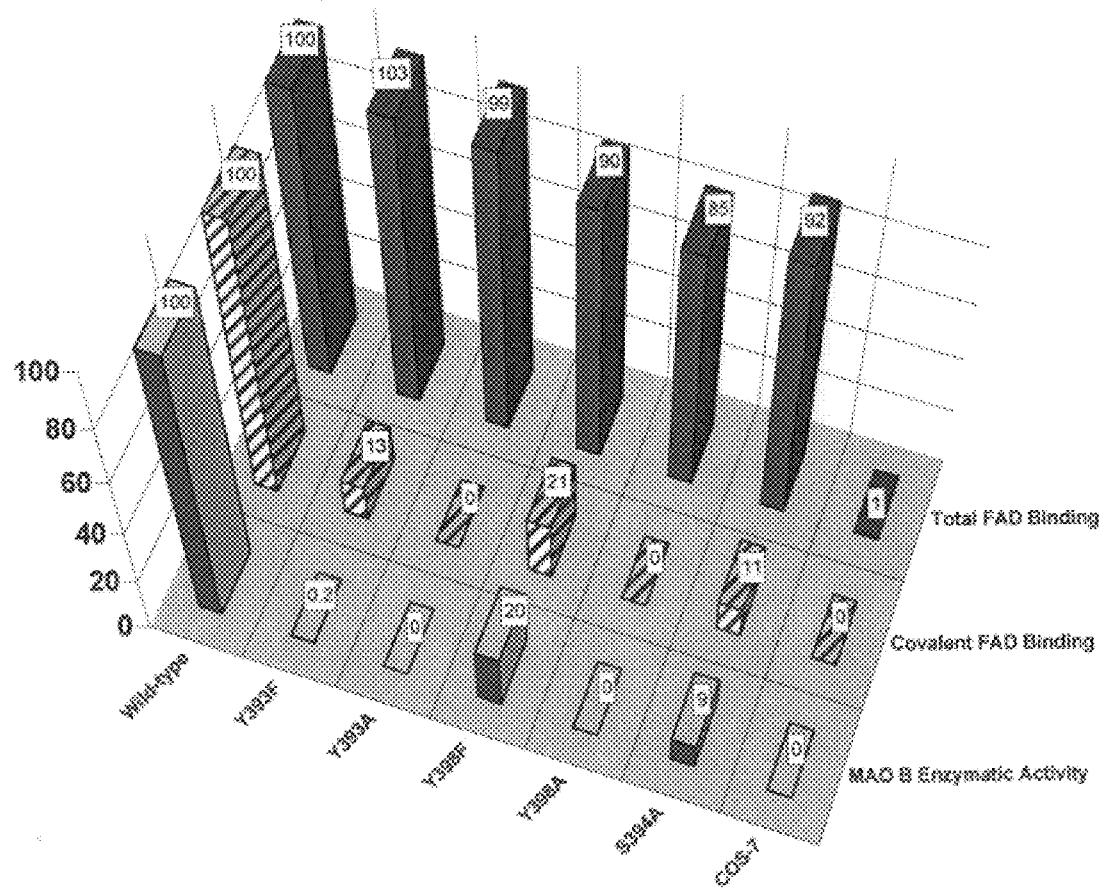

FIG. 5 shows the quantitation of catalytic activities, covalent FAD-binding, and noncovalent FAD-binding in wild-type and variant MAO B proteins. Phosphor screens were exposed to the dried SDS-PAGE and nitrocellulose membrane of dot-blotting for six to ten weeks. The images of the SDS-PAGE and dot-blotting exposed on the screens were then digitized by scanning with a PhosphorImager (Molecular Dynamics, Sunnyvale, Calif.). The digitized images of SDS-PAGE and dot-blotting (as shown in FIG. 4) were quantitated using ImageQuant software (Molecular Dynamics). Enzymatic activity data were taken from Table I. All data are expressed as percent of the corresponding value of wild-type MAO B.

Figure 6:
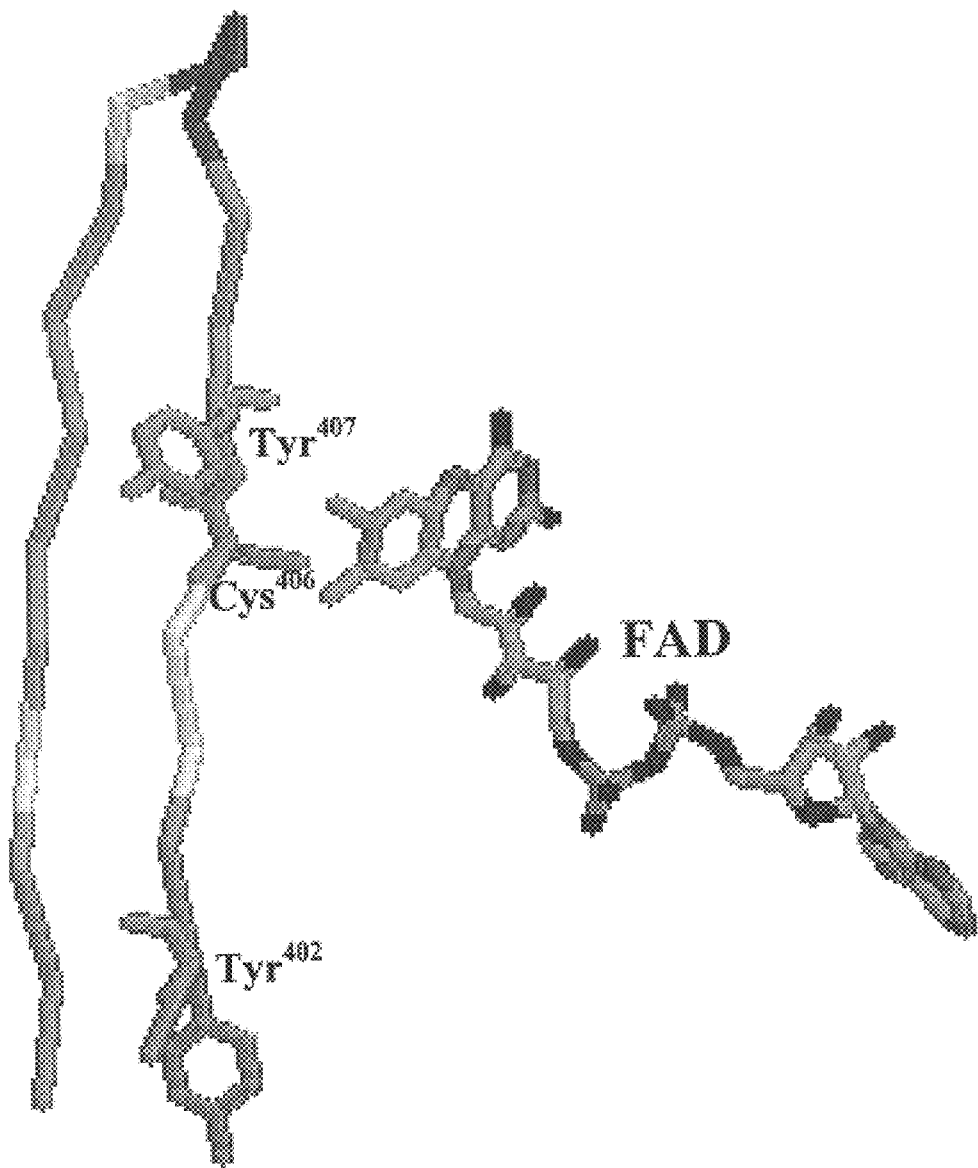

FIG. 6 presents the proposed three-dimensional model for the amino acid sequence flanking the covalent FAD binding residue ($Cys^{406}$) and its relationship with the cofactor FAD in human MAO A (20). The predicted three-dimensional structure of the region flanking $Cys^{406}$ (residues 401–422) is shown. According to this model, a β-strand $Gly^{401}$-$Tyr^{402}$-$Ser^{403}$ preceding the covalent FAD binding residue ($Cys^{406}$) and another β-strand $Gly^{420}$-$Arg^{421}$-$Val^{422}$ several residues downstream of $Cys^{406}$ lie next to each other and extend the covalent FAD binding residue ($Cys^{406}$) and the residue following it ($Tyr^{407}$) into close proximity to the isoalloxazine ring of FAD. β-Strands are shown in yellow. FAD, $Tyr^{402}$, $Cys^{406}$, and $Tyr^{407}$ are labeled, and the side chains of $Tyr^{402}$ (corresponding to $Tyr^{393}$ in MAO B), $Cys^{406}$ (corresponding to $Cys^{397}$ in MAO B) and $Tyr^{407}$ (corresponding to $Tyr^{398}$ in MAO B) are also exhibited. The coordinates of this model were provided by J. Wouters.

DETAILED DESCRIPTION OF THE INVENTION

The present invention is directed toward the amino acid sequence and tertiary structure corresponding to the active site for the monoamine oxidase (MAO) B enzyme and the engineering thereof to achieve neurotransmitter regulation.

As used herein, the terms "Monoamine oxidase" or "MAO" refer to the enzyme responsible for the oxidative deamination, and hence deactivation, of the monoamine neurotransmitters 5-hydroxytryptamine (5HT, serotonin), noradrenaline, and dopamine. Monoamine oxidase also has a role in providing protection from other exogenous (i.e., dietary or environmental) amines that might otherwise have adverse effects on, for example, cardiovascular or neuronal function. Monoamine oxidase exists in two main forms, types A and B; MAO-A (specific inhibitor clorgyline) is responsible for the oxidative removal of serotonin and noradrenaline, whereas in humans, MAO-B (specific inhibitor deprenyl) is the enzyme by which dopamine is mainly metabolized. Both forms of monoamine oxidase are encoded by separate genes on the X chromosome. MAO-B has been shown to activate a protoxin, MPTP, that produces a Parkinsons-like disorder in humans.

As used herein, the term "cytochrome P450" is a collective term for an extensive family of heme-containing electron-transport molecules present in liver microsomes and involved in enzymatic oxidation of a wide range of substrates and their conversion to forms that are more easily excreted. In some cases, the metabolites produced may be carcinogenic. Cytochromes P450 are also involved in the synthesis of compounds such as steroid hormones and prostaglandins. Many of the 200 or so genes that comprise this family are inducible by various exogenous agents. The inducibility shows genetic variability.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment. A vector is said to be "pharmacologically acceptable" if its administration can be tolerated by a recipient mammal.

A "DNA molecule" refers to the polymeric form of deoxyribonucleotides (adenine, guanine, thymine, or cytosine) in either single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a complementary sequence to the mRNA).

A DNA "coding sequence" is a double-stranded DNA sequence which is transcribed into RNA and translated into a polypeptide in vivo when placed under the control of appropriate regulatory sequences. The boundaries of the coding sequence are determined by a start codon at the 5' (amino) terminus and a translational stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Various promoters may be used to drive vectors.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "selection gene" refers to a gene that enables the discrimination of cells displaying a required phenotype upon implementation of certain conditions. For example, the growth of bacteria in medium containing antibiotics to select for the bacterial cells containing antibiotic resistance genes.

The term "oligonucleotide" or "probe" as used herein, refers to a molecule comprised of ribonucleotides or deoxyribonucleotides. The exact size of the oligonucleotide or probe will depend upon many factors which, in turn, depend upon the ultimate function and use of the oligonucleotide.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiments under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, a coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Transcriptional and translational control sequences are DNA regulatory sequences, such as promoters, enhancers, polyadenylation signals, terminators, and the like, that provide for the expression of a coding sequence in a host cell.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J Biol. Chem., 243:3552–59 (1969), abbreviations for amino acid residues are used as is common in the art.

It should be noted that all amino acid sequences are represented herein by formulae whose left and right orientation is in the conventional direction of amino-terminus to carboxy-terminus. Furthermore, it should be noted that a dash at the beginning or end of an amino acid sequence indicates a peptide bond to a further sequence of one or more amino-acid residues.

Comparison of the deduced amino acid sequences of MAO A and B from different species (8, 22–25) reveals three highly conserved regions. These regions reside near the N-terminus, in the middle of the polypeptide, and on each side of the covalent FAD binding residue ($Cys^{397}$) in MAO B. It is hypothesized that the highly conserved region flanking $Cys^{397}$ also plays a role in the covalent binding of FAD. This notion is supported by Wouters & Baudoux (20), who constructed the first partial three-dimensional model of human MAO A based on a combination of primary sequence analysis, secondary structure determination, fold recognition studies, and knowledge-based modeling. This model predicted that $Tyr^{407}$ (corresponding to $Tyr^{398}$ in MAO B) is the only amino acid residue that resides in close proximity to the isoalloxazine ring of FAD in the highly conserved region flanking the covalent FAD binding residue ($Cys^{406}$) in MAOA. Furthermore, Mauch et al. (21) found that $Arg^{67}$ in the sequence $Arg^{67}$-$Ser^{68}$-$Gly^{69}$-$Gly^{70}$ (SEQ ID No.2), which immediately precedes the covalent FAD binding residue (His71), is obligatory for covalent flavinylation of 6-hydroxy-D-nicotine oxidase (6-HDNO). This sequence pattern has also been found in several other flavoproteins with a covalent histidyl(N3)-8α-FAD linkage (FIG. 1).

It is proposed herein that the sequence Tyr393-Ser394-Gly395-Gly396 (SEQ ID No. 3) immediately preceding the covalent FAD binding residue (Cys397) plays a similar role in MAO B as does Arg67-Ser68-Gly69-Gly7O (SEQ ID No.: 2) in 6-HDNO (FIG. 1). To test this hypothesis, variants of human MAO B were made at Tyr393, Ser394 and Tyr398 to examine if these residues participate in the covalent flavinylation of human MAO B. Analysis of these variants demonstrated that the aromatic moieties at Tyr393 and Tyr398 are essential for covalent FAD binding and MAO B catalytic activity.

The present invention is directed towards an isolated, genetically-engineered cellular MAO B enzyme having at least one amino acid substitution for a wild type amino acid near the MAO B active site, where the wild type amino acid is selected from the group of Tyrosine at position 393, Tyrosine at position 398 and Serine at position 394. The present invention additionally provides isolated DNAs that encode these genetically-engineered MAO B enzymes, and plasmids containing these DNAs along with regulatory elements necessary for expression of these DNAs in a cell.

Specific embodiments of this object of the present invention include those where if the wild type amino acid is Tyrosine 393, the amino acid substitution is Alanine or Phenylalanine; where if the wild type amino acid is Tyrosine 398, the amino acid substitution is Alanine or Phenylalanine; and, where if the wild type amino acid is Serine 394, the amino acid substitution is Alanine.

The present invention is also directed towards a pharmaceutical composition which interacts with an active site of MAO B having the sequence SEQ ID No. 1. Furthermore, the pharmaceutical composition may consist of derivative of FAD, derivatives of acetylenic amine inhibitors, derivatives of cyclopropyl amine inhibitors, derivatives of deprenyl (phenylisopropyl-methylproinylamine) and derivatives of trans-phenylcyclopropylamine. The FAD derivative may include 2'-deoxy FAD or 3'-deoxy FAD.

Additionally, an object of the present invention is to provide a method for regulating MAO B comprising the step of mutating an amino acid in the MAO B active site. Specifically, the amino acid to be mutated is selected from the wild type amino acids Tyr 393, Tyr 398, or Ser 394.

Another object of the present invention is to provide a description of the active site of monoamine oxidase B, such that pharmaceutical compositions can be designed to interact with the active site. Specific embodiments of this object of the invention include 2'-deoxy FAD, 3'-deoxy FAD, and derivatives of deprenyl (phenylisopropyl-methylproinylamine) and trans-phenylcyclopropylamine. Molecular modeling is applied to determine which derivatives are most likely to interact with components in the active site of the enzyme.

It will be apparent to one skilled in the art that various substitutions and modifications may be made to the invention disclosed herein without departing from the scope and spirit of the invention. The following examples are given for the purpose of illustrating various embodiments of the invention and are not meant to limit the present invention in any fashion:

EXAMPLE 1
Site-directed Mutagenesis

The Transformer Site-directed Mutagenesis kit (CLONTECH) was used to prepare the appropriate mutant cDNAs (14, 36). Human MAO B cDNA (8) cloned into the EcoRI site of the vector pSVK3 (Pharmacia Biotech, Uppsala, Sweden) was used as the template. The mutagenic primers were designed according to Piechocki and Hines (37) using Gene Runner software (Version 3.04, Hastings Software, Inc.), and the corresponding amino acid changes are shown in FIG. 2. $Tyr^{393}$ and $Tyr^{398}$ were replaced with phenylalanine (Y393F or Y398F) and alanine (Y393A or Y398A). $Ser^{394}$ was also substituted with alanine (S394A).

For purposes of screening, all mutagenic primers were designed to create a new restriction site (in Y398F and Y398A) or to delete a existing restriction site (in Y393F, Y393A and S394A) without altering the coding sequence for any other amino acids. The selection primer was introduced to create a new HpaI restriction site which replaces the sole KpnI site in the plasmid vector. All mutations were confirmed by DNA sequencing using the dideoxy method (38). Both wild-type and mutant plasmid DNAs used in transfection were purified through CsCl gradients.

EXAMPLE 2
Expression of Wild-type and Mutant MAO B cDNAs

COS-7 cells (American Type Culture Collection, Rockville, Md.) were cultured in Dulbecco's modified Eagle's medium (DMEM) with 10% fetal bovine serum (FBS) at 37° C. under a humidified atmosphere of 5% CO2 and 95% air. Riboflavin-depleted COS-7 cells generated earlier (16) were cultured in riboflavin-free DMEM with 10% dialyzed FBS (Life Technologies, Gaithersberg, Md.). The wild-type or mutant MAO B cDNAs (15 µg) transfected into COS-7 cells ($2.5 \times 10^6$ cells in 0.8 ml of medium) by electroporation (39) were transiently expressed (14). In experiments where covalent or noncovalent FAD incorporation of wild-type or variant MAO B proteins was studied, 20 µl of [$^{14}$C] FAD (0.8 mM) and MAO B cDNA (15 µg) were simultaneously electroporated into riboflavin-depleted COS-7 cells ($2.5 \times 10^6$ cells in 0.8 ml of medium). Cells transiently expressing wild-type or variant MAO B were harvested at 48 h following electroporation and homogenized in 300 µl of lysis solution containing 20 mM Tris—HCl, 1.0 mM EDTA, and 0.5 mM PMSF (phenylmethanesulfonyl fluoride), pH 8.0. The wild-type or variant MAO B from each sample was extracted with Triton X-100 at a concentration of 0.25% for 50 min. at 4° C. The supernatant from each sample was collected after centrifugation at 1300× g for 5 min.

EXAMPLE 3
Determination of MAO B Concentration and MAO B Activity

The concentration of wild-type or variant MAO B in each sample was determined using a Micro-BCA kit (Pierce, Rockford, Ill.). All samples were then adjusted to equal protein concentration. MAO B concentration was then quantitated by ELISA (enzyme-linked immunosorbance assay) with a goat polyclonal antibody against MAO B (14, 40).

MAO B activity was measured using a micro-radiochemical assay (14, 41). MAO B activity was expressed both as specific activity (nmol benzylamine/min/mg total protein) and as enzymatic activity (µmol benzylamine/min/mg MAO B).

EXAMPLE 4
Immunoprecipitation of Wild-type and Variant MAO B

Wild-type and variant MAO B proteins were immunoprecipitated as described previously (18). Briefly, equal amounts of wild-type or variant MAO B in each sample as determined by ELISA were brought to the same volume (300 µl), and were incubated with 10 µg of a goat polyclonal anti-MAO B antibody overnight at 4° C. followed by further incubation with 50 µl of immobilized protein G-Sepharose beads for 3 h. The immunocomplexes composed of immobilized protein G-Sepharose, goat antibody, and wild-type/variant MAO B were collected by centrifugation at 10,000× g for 20 sec, and washed 6 times with 20 mM Tris buffer, pH 8.0.

For western blotting and fluorography, the wild-type or variant MAO B proteins in the immunocomplexes were solubilized with 10 µl of SDS-PAGE sample buffer and subsequently analyzed. For dot-blot assays, the wild-type or variant MAO B proteins were eluted from the immunocomplexes with 150 µl of 50 mM glycine, pH 3.0. After a brief spin for 20 sec at room temperature, the supernatant was immediately neutralized by mixing with 20 µl of 1.0 M Tris-HCl buffer, pH 8.0. Elution and neutralization were repeated twice to ensure complete extraction of wild-type or variant MAO B proteins from the immunocomplexes. The eluents were combined for dot-blot assays.

EXAMPLE 5
Western Blot Analysis

Immunoprecipitated proteins were subjected to 10% SDS-PAGE and analyzed by western blotting with the MAO B-specific monoclonal antibody, MAO B-1C2 (10, 14).

EXAMPLE 6
Fluorography

Immunoprecipitated wild-type and variant MAO B enzymes were subjected to electrophoresis in a 10% SDS-PAGE. The gel was fixed (7% acetic acid, 10% methanol) for 1 h and processed for fluorography (16, 42). A phosphor screen was exposed to the dried gel at −80° C. for six weeks. The image exposed on the screen was digitized by scanning with a PhosphorImager (Molecular Dynamics, Sunnyvale, Calif.). The digitized image was quantitated using ImageQuant software (Molecular Dynamics).

EXAMPLE 7
Dot-blot Assays

Immunoprecipitated wild-type and variant MAO B enzymes were analyzed in a dot-blot apparatus (Bio-Rad Laboratories, Hercules, Calif.) according to the manufacturer's instructions as described previously (18). Briefly, each sample, containing immunoprecipitated wild-type or variant MAO B was loaded into an individual well upon a pre-wetted nitrocellulose membrane in a dot-blot apparatus. Proteins were immobilized onto the membrane surface under a gentle vacuum pressure. The wells were washed twice with 150 μl of 20 mM Tris and 1 mM EDTA, pH 8.0. The nitrocellulose membrane was dried in an oven at 50° C. A phosphor screen was exposed to the dried nitrocellulose membrane at −80° C. for ten weeks. The image exposed on the screen was digitized by scanning with a PhosphorImager (Molecular Dynamics, Sunnyvale, Calif.). The digitized image was quantitated using ImageQuant software (Molecular Dynamics).

EXAMPLE 8
Protein Expression and Enzymatic Activities of Variant Proteins

Wild-type and variant MAO B enzymes with substitutions at $Tyr^{393}$, $Tyr^{398}$ and $Ser^{394}$ were transiently expressed in mammalian COS-7 cells which do not contain any detectable endogenous MAO B (14). Expression levels of wild-type and variant MAO B enzymes are shown in Table I.

TABLE I

Comparison of expression levels and catalytic activities of wild-type and variant MAO B proteins

|  | MAO B concentration (ng MAO B/mg protein) | Enzymatic activity (μmol benzylamine/ min/mg MAOB) | Specific activity (nmol benzylamine/min/ mg protein) |
|---|---|---|---|
| Wild-type | 1011 ± 96 (100) | 0.99 ± 0.01 (100) | 0.97 ± 0.05 (100) |
| Y393F | 958 ± 65 (95) | 0.01 ± 0.01 (<1) | 0.01 ± 0.01 (<1) |
| Y393A | 958 ± 60 (95) | 0.01 ± 0.01 (<1) | 0.01 ± 0.01 (<1) |
| Y398F | 1020 ± 58 (101) | 0.20 ± 0.01 (20) | 0.20 ± 0.02 (21) |
| Y398A | 940 ± 64 (93) | 0.00$^b$ ± 0.00 (0) | 0.00 ± 0.00 (0) |
| S394A | 1016 ± 61 (100) | 0.09 ± 0.01 (9) | 0.09 ± 0.01 (9) |

An equal amount of wild-type or variant MAO B cDNA (15 μg) was transiently expressed in COS-7 cells and extracted according to the procedure described in Materials and Methods. After the total protein concentration was equalized in all samples, MAO B quantitation (by ELISA) and activity measurements were performed. Samples were run in duplicates in each experiment. Each value represents the mean ± S.E. from three separate experiments.
$^a$Percent of wild-type values are shown in parentheses.
$^b$Below background level The amount of expressed MAO B for all variants (0.94–1.02 μg MAO B/mg of protein) was similar to that of wild-type MAO B (1.01 μg/mg of protein). The enzymatic activities of MAO B variant proteins Y393F (substitution of $Tyr^{393}$ with phenylalanine) and Y393A (substitution of $Tyr^{393}$ with alanine) were less than 1% of that of wild-type (Table I). The variant protein Y398F (substitution of $Tyr^{398}$ with phenylalanine) retained as much as 20% enzymatic activity of that of wild-type, but the substitution of $Tyr^{398}$ with alanine (Y398A) resulted in a complete loss of enzymatic activity. The variant S394A, where $Ser^{394}$ was replaced with alanine, exhibited 9% enzymatic activity of that of wild-type. Cesura et al. (43) reported that $K_m$ and $K_{cat}$ were 1.99±0.20 μM and 1.68±0.52 s$^{-1}$, respectively, for a variant MAO B protein where $Ser^{394}$ was substituted by alanine, compared to a $K_m$ of 2.45±0.11 μM and $K_{cat}$ of 4.06±0.46 s$^{-1}$, respectively, for wild-type MAO B using embryonic kidney cells (HEK-293) as the expression system. The results herein and those of Cesura et al. (43) both show that the substitution of $Ser^{394}$ by alanine reduces, but does not abolish, the catalytic activity of MAO B. The specific activities of all MAO B variant proteins closely correlated with their enzymatic activities.

EXAMPLE 9
Western Blot Analysis of Immunoprecipitated Proteins

For western blotting assays, immunoprecipitated wild-type and variant MAO B proteins were subjected to SDS-PAGE, and detected using MAO B-1C2 as primary antibody (10). As shown in FIG. 3, wild-type MAO B and all variants have a band of approximately equal intensity at 59 kDa, whereas the sample prepared from untransfected COS-7 cells showed no MAO B band.

EXAMPLE 10
Flavinylation of Variant Proteins

Flavinylation of wild-type and variant MAO B enzymes with substitutions at $Tyr^{393}$, $Tyr^{398}$ and $Ser^{394}$ was studied by simultaneous electroporation of [$^{14}$C] FAD and MAO B cDNA. The quantitatively immunoprecipitated wild-type and variant MAO B proteins were subjected to SDS-PAGE and then fluorography (FIG. 4A). Quantitation of the protein bands on the SDS-PAGE gel showed that covalent incorporation of [$^{14}$C] FAD into Y393F, Y393A, Y398F, Y398A and S394A were 13%, 0%, 21%, 0%, and 11% of that of wild-type, respectively (FIG. 5). These results indicated that variants Y393F, Y398F, and S394A contained low levels of covalently bound FAD, whereas variants Y393A and Y398A showed no covalent binding of FAD.

The total amount of [$^{14}$C] FAD incorporated into MAO B variants includes both covalently linked FAD and noncovalently bound FAD. However, the bands of the wild-type and variant MAO B proteins on the SDS-PAGE gel reflect only covalently bound FAD to the enzyme (FIG. 4A) since noncovalently bound FAD is released from the enzyme due to denaturation of proteins prior to and during SDS-PAGE electrophoresis. Therefore, the dot-blot assay, which was developed in previous studies (18), was used to determine the total amount of [$^{14}$C] FAD incorporated into the wild-type or variant MAO B enzymes, including FAD covalently coupled and non-covalently bound to MAO B. As seen in FIG. 4B, the wild-type and variant enzymes exhibited approximately equal intensities in the dot-blot assay. Quantitation of the total [$^{14}$C] FAD incorporation into the wild-type and variant MAO B proteins showed that the total amounts of FAD (Y393F, Y393A, Y398F, Y398A, and S394A) are 103%, 99%, 90%, 85% and 92% of that of wild-type MAO B, respectively (FIG. 5). These result indicate that the total amount of [$^{14}$C] FAD bound to the apo-enzyme is approximately the same in the wild-type and the variant proteins.

EXAMPLE 11
Mechanism of Covalent Linkage between FAD and MAO B

Previously, it was proposed that flavinylation of MAO B is initiated at a highly conserved region close to the N-terminus which provides a topological dock for the recruitment of FAD (14, 15, 17). An important intermediate step involves noncovalent FAD binding to a site (residues 2–227 in MAO B) that is located at the end of a highly conserved region in the middle of the MAO B. Subsequently, the 8α-methyl group of the isoalloxazine ring of FAD is brought into close proximity to the thiol group of $Cys^{397}$ to facilitate the covalent linkage between FAD and the MAO B polypeptide. Based on the data provided herein, it is now proposed that the highly conserved region flanking the covalent FAD binding residue ($Cys^{397}$) also participates in MAO B flavinylation (see FIG. 1). This possibly facilitates the formation of the covalent linkage between the 8α-methyl group of the isoalloxazine ring of FAD and $Cys^{397}$ of MAO B polypeptide.

EXAMPLE 12
Amino Acid Sequences Surrounding Flavinylation Sites

More than 20 covalent flavoproteins have been identified (44, 45) in which the cofactor FAD or FMN is covalently linked to a cysteine, histidine, or tyrosine residue. There is no apparent sequence homology in the region flanking the covalent FAD binding residue among these covalent flavoproteins (46). However, Mauch et al. (21) observed a unique amino acid sequence Arg-Ser-Gly-Gly (Seq ID No. 4) immediately preceding the covalent FAD binding residue (a histidine) in some covalent flavoproteins where the 8α-methyl group of FAD is linked to the N3 atom of histidine (FIG. 1). Furthermore, $His^{71}$, which is covalently linked to FAD, is followed by a polar amino acid residue (serine, threonine, or asparagine) among these flavoproteins with a covalent histidyl(N3)-8α-FAD linkage. Using site-directed mutagenesis, Mauch et al. (21) found that a basic residue at position 67 in the sequence $Arg^{67}$-$Ser^{68}$-$Gly^{69}$-$Gly^{70}$ (SEQ ID No.: 2) immediately preceding the covalent FAD binding residue ($His^{71}$) is obligatory for covalent flavinylation in 6-HDNO. Their results also indicated that $Arg^{67}$ is involved not only in 6-HDNO flavinylation but also in generating 6-HDNO catalytic activity. Furthermore, they found that a serine residue at position 68 is not essential for 6-HDNO flavinylation and activity.

An analogous sequence pattern was observed flanking the covalent FAD binding residue in the covalent flavoproteins where the 8α-methyl group of FAD is covalently linked to a cysteine residue through a thioether linkage (FIG. 1). In flavoproteins with a covalent cysteinyl(S)-8 α-FAD linkage, the cysteine residue which is covalently linked to FAD is preceded by the sequence Tyr-Ser-Gly-Gly (SEQ ID No. 5), and followed by a tyrosine residue ($Tyr^{398}$). To examine the role of the sequence flanking the covalent FAD binding residue ($Cys^{397}$) in human MAO B, $Tyr^{393}$, $Ser^{394}$ and $Tyr^{398}$ were substituted with structurally similar amino acids (FIG. 2) and tested for FAD noncovalent and covalent binding and catalytic activity.

EXAMPLE 13
Effects of Amino Acid Substitutions on MAO B Activity

Substitutions of $Tyr^{393}$ and $Tyr^{398}$ with alanine (Y393A and Y398A) abolished covalent FAD binding completely, whereas Y393F and Y398F partially retained their capacity to bind FAD covalently (13% and 21% of that of wide-type MAO B, respectively) (FIG. 5). These results indicate that the aromatic and/or hydroxyl moieties of $Tyr^{393}$ and $Tyr^{398}$ are required for covalent FAD binding in MAO B. Replacement of $Ser^{394}$ with alanine (S394A) markedly reduced, but did not eliminate, enzymatic activity (9% of wild-type) and covalent FAD binding (11% of the wide-type). Since this substitution did not result in complete loss of covalent FAD binding and enzymatic activity, this suggests that the hydroxyl side chain of $Ser^{394}$ does not play a major role in the maturation of catalytically active enzyme.

EXAMPLE 14
The Relationship between MAO B Catalytic Activity and FAD

For variant proteins at $Ser^{394}$ and $Tyr^{398}$, there is a good correlation between catalytic activity and covalent FAD binding (FIG. 5) which is in agreement with previous work (18) and reports from other laboratories (47–49). This result supports the concept that covalent FAD binding is obligatory for MAO B catalytic activity in MAO B (18). Interestingly, Y393F lost catalytic activity almost completely (0.2% of wild-type) though it retained somehow covalent FAD binding (13% of wild-type). One interpretation is that FAD covalent binding is necessary but not sufficient for the generation of catalytic activity. Conformational changes in the active site may be required after apo-MAO B is converted to the flavoenzyme. For example, the positioning of the hydroxyl group on the side chain of $Tyr^{393}$ may be essential for MAO B catalytic activity, although it is not obligatory for covalent FAD binding in MAO B. It is possible that FAD could be tightly bound to Cys397 in a conformation that would not support catalytic activity.

Interestingly, substitutions at $Tyr^{393}$, $Ser^{394}$ and $Tyr^{398}$ did not substantially reduce the ability of the variant proteins to bind FAD noncovalently (FIG. 5). The residues flanking the covalent FAD binding residue ($Cys^{397}$) apparently have little or no impact on noncovalent FAD binding, despite the fact that they facilitate covalent FAD binding and generation of MAO B catalytic activity. These results support the notion that MAO B flavinylation is a stepwise process including early steps to bind FAD noncovalently and later steps to link FAD covalently (18). In this process, the tyrosine residues flanking the covalent FAD binding residue ($Cys^{397}$) may only participate in the later steps of MAO B flavinylation to form the covalent linkage between FAD and MAO B polypeptide.

EXAMPLE 15
MAO B Amino Acid Substitutions and the Three Dimensional Structure of MAO A Recently, Wouters and Baudoux (20) constructed the first partial three-dimensional model of human MAO A. The presence of predicted motifs in the three-dimensional structure in this model is supported by several lines of experimental data (14–17, 47–49). The covalent FAD binding residue ($Cys^{406}$) (corresponding to $Cys^{397}$ in MAO B) has been predicted to be in close proximity to the isoalloxazine ring of FAD. Furthermore, $Tyr^{407}$ (corresponding to $Tyr^{398}$ in MAO B), which immediately follows $Cys^{406}$, is the only residue close to the isoalloxazine ring of FAD in the highly conserved region flanking the covalent FAD binding residue ($Cys^{406}$) (FIG. 6). Due to a high degree of amino acid sequence identity in MAO A and B (approximately 70%), MAO B presumably may have a three-dimensional structure similar to MAO A. Based on the result herein, it is proposes that the aromatic moiety of $Tyr^{398}$ directly interacts with the isoalloxazine ring of FAD to assist the alignment of the 8α-methyl group of the isoalloxazine ring of FAD with the thiol group of $Cys^{397}$ to facilitate the covalent linkage between FAD and the MAO B polypeptide. This interpretation is supported by the finding that $Tyr^{398}$ is necessary for FAD to covalently bind to MAO B. Substitution of $Tyr^{398}$ with $Phe^{398}$ resulted in a loss of most (80%) but not all of the activity. This suggests that the hydroxyl group may play some role at the FAD binding site.

In the three-dimensional model of MAO A, $Tyr^{402}$ (corresponding to $Tyr^{393}$ in MAO B) is more distally located from FAD (FIG. 6). It is unlikely that $Tyr^{393}$ in MAO B could directly interact with FAD according to this model, though the site-directed mutagenesis studies indicate that the aromatic moiety and/or hydroxyl group at $Tyr^{393}$ is mandatory for covalent FAD binding in MAO B. It seems that $Tyr^{393}$ plays an indirect role in assisting the covalent flavinylation of MAO B, in contrast to the possibly direct interaction between $Tyr^{398}$ and FAD in MAO B.

EXAMPLE 16
Antiparallel β-Strands Surround Flavinylation Site

In the three-dimensional model of MAO A proposed by Wouters and Baudoux (20), a short β-strand $Gly^{401}$-$Tyr^{402}$-$Ser^{403}$ preceding the covalent FAD binding residue $Cys^{406}$ and another short β-strand $Gly^{420}$-$Arg^{421}$-$Val^{422}$ located 13 residues downstream of $Cys^{406}$ lie next to each other in an antiparallel orientation (FIG. 6). These short β-strands correspond to sequences $Gly^{392}$-$Tyr^{393}$-$Ser^{394}$ and $Gly^{411}$-$Arg^{412}$-$Val^{413}$ in MAO B (FIG. 1). Since FCSD is the only Cys flavoprotein (FIG. 1) whose structure has been solved (27), comparison of its amino acid sequence and structure with that in MAO B is particularly illuminating. In FCSD, a short β-strand $Tyr^{39}$-$Tyr^{40}$-$Thr^{41}$ precedes the covalent FAD binding residue ($Cys^{42}$) and another short β-strand $Ile^{58}$-$Lys^{59}$-$His^{60}$ aligns in a antiparallel fashion (26). The two short β-strands flanking the covalent FAD binding residue (a cysteine) lie next to each, and play a crucial role in covalent FAD binding in flavoproteins with a covalent cysteinyl(S)-8α-FAD linkage. Repetitive glycine and proline residues, i.e., a conserved sequence Pro-Pro-Gly in MAO A and B or a sequence Gly-Gly in FCSD, often reside in non-periodic secondary structures such as loops and turns (FIG. 1). A loop initiated by repetitive glycine and proline residues is necessary for two short β-strands only several amino acid residues apart to be able to lie next to each other in these covalent flavoproteins. A conserved tyrosine is found as the second amino acid residue in the β-strand preceding the covalent FAD binding residue (Cys). A scaffold formed by the two antiparallel β-strands extends the covalent FAD binding residue (a cysteine) and a tyrosine residue (immediately following the cysteine) to interact with the isoalloxazine ring of FAD. The examples provided herein show that the aromatic moiety of the residue ($Tyr^{398}$) immediately following the covalent FAD binding residue ($Cys^{397}$) is probably important for covalent FAD binding in MAO B, since substitution with phenylalanine retains some activity (20%) (FIG. 4a, FIG. 5).

EXAMPLE 17
Conservation of Gly-Gly Sequence in Flavoproteins with a Covalent Histidyl(N3)-8α-FAD Linkage In flavoproteins with a covalent histidyl(N3)-8α-FAD linkage, a sequence of Gly-Gly is also located several amino acid residues downstream from the covalent FAD binding residue. In a spontaneous *Bacillus subtilis* mutant, Maguire et al. (50) found that substitution of $Gly^{47}$ by an aspartate residue, which is seven residues downstream of the covalent FAD binding residue ($His^{40}$), abolished the ability of SDHA to bind FAD covalently, suggesting that the conservation of this glycine residue is essential for covalent FAD binding. It is possible that flavoproteins with a covalent histidyl(N3)-8α-FAD linkage adapt a structural motif flanking their covalent FAD binding residue (a histidine) analogous to that of the flavoproteins with a covalent cysteinyl(S)-8α-FAD linkage, where the conserved sequence Gly-Gly downstream from the covalent FAD residue (a histidine) resides in the loop region of the structural motif. For these flavoproteins with a covalent histidyl(N3)-8α-FAD linkage, however, the conserved second residue in the proposed β-strand preceding the covalent FAD binding residue (a histidine) is a basic residue instead of an aromatic one (21). The residue immediately following the covalent FAD bound residue (a histidine) is conserved as a polar residue (serine, or threonine, or asparagine) in these flavoproteins, instead of an aromatic residue as in the flavoproteins with a covalent cysteinyl(S)-8α-FAD linkage.

EXAMPLE 18
FAD Binding Amino Acids and Adjacent Residues

For the flavoproteins with a covalent cysteinyl(S)-8α-FAD linkage in FIG. 1, the covalent FAD binding residue (a cysteine) is polar and the residue immediately following it is aromatic. For the flavoproteins with covalent histidyl(N3)-8α-FAD linkage in FIG. 1, the covalent FAD binding residue (a histidine) is aromatic and the residue immediately following it is polar. Collectively, the covalent FAD binding residue (a cysteine, or a histidine) and the residue immediately following it are extended out by the scaffold of the two antiparallel β-strands to interact with the isoalloxazine ring of FAD in these covalent flavoproteins. These two residues are polar and aromatic, respectively (FIG. 1). This feature could be important for the polypeptide to interact with the isoalloxazine ring of FAD effectively in order to form the covalent linkage between the polypeptide and the FAD molecule.

It has been reported that the variant MAO B enzyme in which the covalent FAD binding residue ($Cys^{397}$) is substituted with a histidine residue is catalytically inactive, presumably due to its inability to bind FAD covalently (47, 49). Conversely, the variant 6-HDNO protein in which covalent FAD binding residue ($His^{71}$) is replaced by a cysteine residue also loses its ability to bind FAD covalently (51).

The results of this study and previous studies (14–18) provide important insight into the process of MAO B flavinylation. The results herein demonstrate that the highly conserved sequence flanking the covalent FAD binding residue ($Cys^{397}$) plays a crucial role in this process. This suggests that a scaffold of two antiparallel β-strands formed by this sequence assists in the formation of the covalent linkage between FAD and MAO B polypeptide, where the aromatic moieties at both $Tyr^{393}$ and $Tyr^{398}$ in this sequence are mandatory for covalent FAD binding in MAO B although the mechanism for them to interact with the FAD molecule may be different. It is possible that this structural motif flanking the covalent FAD binding residue (a cysteine, or a histidine) is conserved in a family of covalent flavoproteins with a covalent cysteinyl(S)-8α-FAD linkage or a covalent histidyl(N3)-8α-FAD linkage, although their primary sequences do not appear homologous in this region.

The following references were cited herein:
1. Greenawalt, et al., (1970) *J. Cell. Biol.* 46, 173–179
2. Von Korff, et al., (1979) in *Monoamine oxidase: Structure, Function, and Altered functions* (Singer, T. P., Von Korff, R., and Murphy, D., eds) pp. 1–7, Academic Press, Inc.,
3. Chiba, et al., (1984) *Biochem. Biophys. Res. Commun.* 120, 574–578
4. Westlund, et al., (1988) *Neurosci.* 25, 439–456.
5. Da Prada, et al., (1989) *J.Neural Transm.* 28, 5–20
6. Tetrud, J. W. and Langston, J. W. (1989) *Science* 245, 519–522
7. Devor, et al., (1993) *Alcohol.Clin.Exp.Res.* 17, 263–267
8. Bach, et al., (1988) *Proc. Natl. Acad. Sci. USA* 85, 4934–4938
9. Weyler, W. (1989) *Biochem. J.* 260, 725–729
10. Denney, et al., (1982) *Science* 215, 1400–1403
11. Kochersperger, et al., (1985) *J. Neurosci.* 5, 2874–2881
12. Westlund, et al., (1985) *Science* 230, 181–183
13. Dostert, et al., (1989) *Med. Res. Rev.* 9, 45–89
14. Kwan, et al., (1995) *Arch. Biochem. Biophys.* 316, 385–391
15. Zhou, et al., (1995) *Biochemistry* 34, 9526–9531
16. Zhou, et al., (1995) *J. Biol. Chem.* 270, 23653–23660
17. Kirksey, et al., (1998) *Biochemistry* 37, 12360–12366
18. Zhou, et al., (1998) *J. Biol. Chem.* 273, 14862–14868
20. Wouters, J. and Baudoux, G. (1998) *Proteins* 32, 97–110

21. Mauch, et al., (1990) *J. Biol. Chem.* 265, 12761–12762
22. Kuwahara, et al., (1990) *Agric. Biol. Chem.* 54, 253–259
23. Kwan, et al., (1992) *Comp. Biochem. Physiol* 102B, 143–147
24. Powell, et al., (1989) *Biochem. J.* 259, 407–413
25. Ito et al., (1988) *Biochem. Biophys. Res. Commun.* 157, 970–976
26. Van Driessche, et al., (1996) *Prot. Sci.* 5, 1753–1764
27. Chen, et al., (1994) *Science* 266, 430–432
28. Brandsch, et al., (1987) *Eur. J. Biochem.* 167, 315–320
29. Birch-Machin, et al., (1992) *J. Biol. Chem.* 267, 11553–11558
30. Robinson, et al., (1992) *J. Biol. Chem.* 267, 10101–10107
31. Wood, et al., (1984) *Biochem. J.* 222, 519–534
32. Phillips et al., (1987) *J. Bacteriol* 169, 864–873
33. Cole, S. T. (1987) *Eur. J. Biochem.* 167, 481–488
34. Cole, S. T. (1982) *Eur J Biochem* 122, 479–484
35. Lauterbach, et al., (1990) *Arch. Microbiol.* 154, 386–393
36. Deng, W. and Nickoloff, J. (1992) *Anal. Biochem.* 200, 81–88
37. Piechocki, et al., (1994) *BioTechniques* 16, 702–707
38. Sanger et al., (1977) *Proc. Natl. Acad. Sci. USA* 74, 5463–5467
39. Zimmerman, et al., (1982) *J. Membr. Biol.* 67, 165–182
40. Yeomanson, et al., (1992) *Biochim.Biophys. Acta.* 1116, 261–268
41. Wurtman, et al., (1963) *Biochem. Pharmacol.* 12, 1439–1440
42. Bonner, W. and Laskey, R. (1974) *Eur. J. Biochem.* 46, 83–88
43. Cesura, et al., (1996) *Eur. J. Biochem.* 236, 996–1002
44. Abell, et al., (1994) *Heterocycles* 39, 933–955
45. Mewies, et al., (1998) *Prot. Sci.* 7, 7–20
46. Decker, K. (1991) in *Chemistry and Biochemistry of Flavoenzymes* (Muller, F., ed) pp. 343–375, CRC Press, Boca Raton, Fla.
47. Gottowik, et al., (1993) *FEBS Letters* 317, 152–156
48. Wu, et al., (1993) *Mol. Pharmacol.* 43, 888–893
49. Ogata, et al., (1994) in *Flavin and Flavoproteins* 1993 (Yagi, K., ed) pp. 795–798, Walter de Gruyter & Co., Berlin
50. Maguire, et al., (1986) *Biochemistry* 25, 5202–5208
51. Mauch, et al., (1989) *FEBS Lett.* 257, 86–88

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated, mutated human monoamine oxidase B (MAO B) enzyme having at least one amino acid substitution, which is different relative to the wild type amino acids in a MAO B active site, wherein said wild type amino acid is selected from the group consisting of Tyr$^{393}$ and Tyr$^{398}$.

2. An isolated DNA encoding the isolated MAO B enzyme of claim 1.

3. A plasmid containing said DNA of claim 2 and regulatory elements necessary for expression of said DNA in a cell.

4. The enzyme of claim 1, wherein alanine is substituted for Tyr393 of the wild type enzyme.

5. The enzyme of claim 1, wherein phenylalanine is substituted for Tyr 393 of the wild type enzyme.

6. The enzyme of claim 1, wherein alanine is substituted for Tyr398 of the wild type enzyme.

7. The enzyme of claim 1, wherein phenylalanine is substituted for Tyr 398 of the wild type enzyme.

* * * * *

UNITED STATES PATENT AND TRADEMARK OFFICE
CERTIFICATE OF CORRECTION

PATENT NO. : 6,440,714 B2
DATED : August 27, 2002
INVENTOR(S) : Creed W. Abell et al.

It is certified that error appears in the above-identified patent and that said Letters Patent is hereby corrected as shown below:

<u>Column 4,</u>
Line 21, "present" should read -- presents --.

<u>Column 12,</u>
Line 51, "result" should read -- results --.

<u>Column 14,</u>
Line 47, "proposes" should read -- proposed --.

<u>Column 15,</u>
Line 16, "a antiparallel" should read -- an antiparallel --.
Line 52, "bistidyl" should read -- histidyl --.

Signed and Sealed this

Second Day of March, 2004

JON W. DUDAS
*Acting Director of the United States Patent and Trademark Office*

SEQUENCE LISTING

```
<160> NUMBER OF SEQ ID NOS: 26

<210> SEQ ID NO 1
<211> LENGTH: 17
<212> TYPE: PRT
<213> ORGANISM: Homo sapiens
<220> FEATURE:
<223> OTHER INFORMATION: Amino acid sequence of active site of wild type
      MAO B enzyme

<400> SEQUENCE: 1

Asp Arg Ile Tyr Phe Ala Gly Thr Glu Thr Ala Thr His Trp Ser
              5                   10                  15
Gly Tyr

<210> SEQ ID NO 2
<211> LENGTH: 4
<212> TYPE: PRT
<213> ORGANISM: A. oxidans
<220> FEATURE:
<223> OTHER INFORMATION: Amino acid sequence (residues 67-70) preceding
      covalent FAD binding residue (His 71) of 6-
      hydroxy-D-nicotine oxidase (6-HDNO)

<400> SEQUENCE: 2

Arg Ser Gly Gly

<210> SEQ ID NO 3
<211> LENGTH: 4
<212> TYPE: PRT
<213> ORGANISM: Homo sapiens
<220> FEATURE:
```

```
<222> LOCATION: 393..396
<223> OTHER INFORMATION: Amino acid sequence immediately preceding the
      covalent FAD binding residue (Cys 397) of
      monoamine oxidase B

<400> SEQUENCE: 3

Tyr Ser Gly Gly

<210> SEQ ID NO 4
<211> LENGTH: 4
<212> TYPE: PRT
<213> ORGANISM: Unknown
<220> FEATURE:
<223> OTHER INFORMATION: Consensus sequence preceding the covalent FAD
      binding residue ( histidine) in some covalent
      flavoproteins where the 8a-methyl group of FAD
      is linked to the N3 atom of histidine.

<400> SEQUENCE: 4

Arg Ser Gly Gly

<210> SEQ ID NO 5
<211> LENGTH: 4
<212> TYPE: PRT
<213> ORGANISM: Unknown
<220> FEATURE:
<223> OTHER INFORMATION: Consensus sequence preceding the covalent FAD
      binding residue (cysteine) in covalent flavo-
      proteins; the 8(-methyl group of FAD is linked
      to a cysteine residue by a thioether linkage.

<400> SEQUENCE: 5

Tyr Ser Gly Gly

<210> SEQ ID NO 6
<211> LENGTH: 22
<212> TYPE: PRT
<213> ORGANISM: Homo sapiens
<220> FEATURE:
<221> NAME/KEY: FAD binding residue (a cysteine)
<223> OTHER INFORMATION: Amino acid sequence flanking the covalent FAD
      binding residue of human monooxidase A (MAO A)

<400> SEQUENCE: 6

Gln Tyr Ser Gly Gly Cys Tyr Thr Ala Tyr Phe Pro Pro Gly Ile
                 5                  10                  15

Met Thr Gln Tyr Gly Arg Val
             20

<210> SEQ ID NO 7
<211> LENGTH: 22
<212> TYPE: PRT
<213> ORGANISM: Rattus Norwegicus
<220> FEATURE:
<223> OTHER INFORMATION: Amino acid sequence flanking the covalent FAD
      binding residue of rat monooxidase A (MAO A)

<400> SEQUENCE: 7

Gln Tyr Ser Gly Gly Cys Tyr Thr Ala Tyr Phe Pro Pro Gly Ile
                 5                  10                  15

Met Thr Gln Tyr Gly Arg Val
             20

<210> SEQ ID NO 8
<211> LENGTH: 22
<212> TYPE: PRT
<213> ORGANISM: Bos taurus
```

```
<220> FEATURE:
<223> OTHER INFORMATION: Amino acid sequence flanking the covalent FAD
      binding residue of bovine monooxidase A (MAO A)

<400> SEQUENCE: 8

Gln Tyr Ser Gly Gly Cys Tyr Thr Ala Tyr Phe Pro Pro Gly Ile
                 5                  10                  15

Met Thr Gln Tyr Gly Arg Val
            20

<210> SEQ ID NO 9
<211> LENGTH: 22
<212> TYPE: PRT
<213> ORGANISM: Homo sapiens
<220> FEATURE:
<223> OTHER INFORMATION: Amino acid sequence flanking the covalent FAD
      binding residue of human monooxidase B (MAO B)

<400> SEQUENCE: 9

Gln Tyr Ser Gly Gly Cys Tyr Thr Thr Tyr Phe Pro Pro Gly Ile
                 5                  10                  15

Leu Thr Gln Tyr Gly Arg Val
            20

<210> SEQ ID NO 10
<211> LENGTH: 22
<212> TYPE: PRT
<213> ORGANISM: Rattus norwegicus
<220> FEATURE:
<223> OTHER INFORMATION: Amino acid sequence flanking the covalent FAD
      binding residue of rat monooxidase B (MAO B)

<400> SEQUENCE: 10

Gln Tyr Ser Gly Gly Cys Tyr Thr Ala Tyr Phe Pro Pro Gly Ile
                 5                  10                  15

Leu Thr Gln Tyr Gly Arg Val
            20

<210> SEQ ID NO 11
<211> LENGTH: 22
<212> TYPE: PRT
<213> ORGANISM: C. vinosium
<223> OTHER INFORMATION: Amino acid sequence flanking the covalent FAD

<400> SEQUENCE: 11

Tyr Tyr Thr Cys Tyr Leu Ser Asn Glu Val Ile Gly Gly Asp Arg
                 5                  10                  15

Lys Leu Glu Ser Ile Lys His
            20

<210> SEQ ID NO 12
<211> LENGTH: 27
<212> TYPE: PRT
<213> ORGANISM: A oxidans
<220> FEATURE:
<223> OTHER INFORMATION: Amino acid sequence flanking the covalent FAD
      binding residue of A oxidans 6-hydroxy-D-
      nicotine oxidase (6-HDNO)

<400> SEQUENCE: 12

Val Arg Ser Gly Gly His Asn Pro Asn Gly Tyr Ala Thr Asn Asp
                 5                  10                  15

Gly Gly Ile Val Leu Asp Leu Arg Leu Met Asn Ser
            20                  25
```

```
<210> SEQ ID NO 13
<211> LENGTH: 19
<212> TYPE: PRT
<213> ORGANISM: Bos taurus
<220> FEATURE:
<223> OTHER INFORMATION: Amino acid sequence flanking the covalent
      FAD binding residue of bovine succinate
      dehydrogenase (SDHA)

<400> SEQUENCE: 13

Thr Arg Ser His Thr Val Ala Ala Gln Gly Gly Ile Asn Ala Ala
                 5                  10                  15

Leu Gly Asn Met

<210> SEQ ID NO 14
<211> LENGTH: 19
<212> TYPE: PRT
<213> ORGANISM: S. cerevisiae
<220> FEATURE:
<223> OTHER INFORMATION: Amino acid sequence flanking the covalent FAD
      binding residue of S. cerevisiae succinate
      dehydrogenase (SDHA)

<400> SEQUENCE: 14

Thr Arg Ser His Thr Val Ala Ala Gln Gly Gly Ile Asn Ala Ala
                 5                  10                  15

Leu Gly Asn Met

<210> SEQ ID NO 15
<211> LENGTH: 19
<212> TYPE: PRT
<213> ORGANISM: E. coli
<220> FEATURE:
<223> OTHER INFORMATION: Amino acid sequence flanking the covalent FAD
      binding residue of E. coli succinate
      dehydrogenase (SDHA)

<400> SEQUENCE: 15

Thr Arg Ser His Thr Val Ser Ala Gln Gly Gly Ile Thr Val Ala
                 5                  10                  15

Leu Gly Asn Thr

<210> SEQ ID NO 16
<211> LENGTH: 18
<212> TYPE: PRT
<213> ORGANISM: B. subtilis
<220> FEATURE:
<223> OTHER INFORMATION: Amino acid sequence flanking the covalent FAD
      binding residue of B. subtilis succinate
      dehydrogenase (SDHA)

<400> SEQUENCE: 16

Lys Arg Ser His Ser Val Cys Ala Gln Gly Gly Ile Asn Gly Ala
                 5                  10                  15

Val Asn Thr

<210> SEQ ID NO 17
<211> LENGTH: 18
<212> TYPE: PRT
<213> ORGANISM: P. vulgaris
<220> FEATURE:
<223> OTHER INFORMATION: Amino acid sequence flanking the covalent FAD
      binding residue of P. vulgaris fumarate
      reductase (FRDA)

<400> SEQUENCE: 17
```

Met Arg Ser His Thr Val Ala Ala Glu Gly Gly Ser Ala Ala Val
                  5                   10                  15

Thr Gln Ala

<210> SEQ ID NO 18
<211> LENGTH: 18
<212> TYPE: PRT
<213> ORGANISM: E. coli
<220> FEATURE:
<223> OTHER INFORMATION: Amino acid sequence flanking the covalent FAD
      binding residue of E. coli fumarate reductase
      (FRDA).

<400> SEQUENCE: 18

Met Arg Ser His Thr Val Ala Ala Glu Gly Gly Ser Ala Ala Val
                  5                   10                  15

Ala Gln Asp

<210> SEQ ID NO 19
<211> LENGTH: 19
<212> TYPE: PRT
<213> ORGANISM: W. succinogenes
<220> FEATURE:
<223> OTHER INFORMATION: Amino acid sequence flanking the covalent FAD
      binding residue of W. succinogenes fumarate
      reductase (FRDA).

<400> SEQUENCE: 19

Lys Arg Ser His Ser Ala Ala Ala Gln Gly Gly Met Gln Ala Ser
                  5                   10                  15

Leu Gly Asn Ser

<210> SEQ ID NO 20
<211> LENGTH: 17
<212> TYPE: PRT
<213> ORGANISM: Homo sapiens
<220> FEATURE:
<223> OTHER INFORMATION: Amino acid sequence flanking the covalent FAD
      binding residue of human monooxidase B (MAO B)

<400> SEQUENCE: 20

Trp Cys Glu Glu Gln Tyr Ser Gly Gly Cys Tyr Thr Thr Tyr Phe
                  5                   10                  15

Pro Pro

<210> SEQ ID NO 21
<211> LENGTH: 51
<212> TYPE: DNA
<213> ORGANISM: Homo Sapiens
<220> FEATURE:
<223> OTHER INFORMATION: Nucleotide sequence encoding the covalent FAD
      binding site of human monooxidase B (MAO B)

<400> SEQUENCE: 21
tggtgtgagg agcagtactc tgggggctgc tacacaactt atttcccccc         50
t                                                             51

<210> SEQ ID NO 22
<211> LENGTH: 28
<212> TYPE: DNA
<213> ORGANISM: artificial sequence
<220> FEATURE:
<223> OTHER INFORMATION: Nucleotide sequence of mutagenic primer
      used to construct Y393F cDNA

<400> SEQUENCE: 22
ggtgtgagga gcagttctct gggggctg                                28

<210> SEQ ID NO 23
<211> LENGTH: 28
<212> TYPE: DNA
<213> ORGANISM: artificial sequence
<220> FEATURE:
<223> OTHER INFORMATION: Nucleotide sequence of mutagenic primer
      used to construct Y393A cDNA

<400> SEQUENCE: 23
ggtgtgagga gcaggcctct gggggctg                                28

<210> SEQ ID NO 24
<211> LENGTH: 21
<212> TYPE: DNA
<213> ORGANISM: artificial sequence
<220> FEATURE:
<223> OTHER INFORMATION: Nucleotide sequence of mutagenic primer
      used to construct S394A cDNA

<400> SEQUENCE: 24
ggagcagtac gctgggggct g                                       21

<210> SEQ ID NO 25
<211> LENGTH: 27
<212> TYPE: DNA
<213> ORGANISM: artificial sequence
<220> FEATURE:
<223> OTHER INFORMATION: Nucleotide sequence of mutagenic primer
      used to construct Y398F cDNA

<400> SEQUENCE: 25
gggctgcttc actacgtatt tcccccc                                 27

<210> SEQ ID NO 26
<211> LENGTH: 28
<212> TYPE: DNA
<213> ORGANISM: artificial sequence
<220> FEATURE:
<223> OTHER INFORMATION: Nucleotide sequence of mutagenic primer
      used to construct Y398A cDNA

<400> SEQUENCE: 26
ctgggggctg cgcaacaact tatttccc                                28